United States Patent
Dickey et al.

[11] Patent Number: 5,821,405
[45] Date of Patent: Oct. 13, 1998

[54] MODULAR WATER QUALITY APPARATUS AND METHOD

[75] Inventors: Terry Lee Dickey, Pflugerville; Michael Albert Alkier, Austin, both of Tex.

[73] Assignee: Hydrolab Corporation, Austin, Tex.

[21] Appl. No.: 911,213

[22] Filed: Aug. 14, 1997

Related U.S. Application Data

[63] Continuation of Ser. No. 608,710, Feb. 29, 1996, abandoned.

[51] Int. Cl.[6] .............................. G01N 11/00; G01G 5/00; G01D 11/24; G01D 21/00
[52] U.S. Cl. .................... 73/53.01; 73/170.29; 73/866.5; 73/431
[58] Field of Search ................ 73/19.01, 53.01, 73/170.29, 866.5, 431; 364/509, 550

[56] References Cited

U.S. PATENT DOCUMENTS

| | | | |
|---|---|---|---|
| 2,756,404 | 7/1956 | Anderson et al. | 73/53.01 |
| 3,762,214 | 10/1973 | Bogusz | 73/170.29 |
| 4,287,764 | 9/1981 | Staab et al. | 73/431 |
| 4,662,210 | 5/1987 | D'Aoust | 73/19 |
| 4,870,863 | 10/1989 | Duncan et al. | 73/431 |
| 5,121,627 | 6/1992 | D'Aoust | 73/19.05 |
| 5,140,855 | 8/1992 | Gruber | 73/432.1 |
| 5,172,332 | 12/1992 | Hungerford et al. | 364/571 |
| 5,415,038 | 5/1995 | Rynhat et al. | 73/431 |
| 5,471,885 | 12/1995 | Wagner | 73/431 |
| 5,517,646 | 5/1996 | Piccirillo et al. | 395/700 |
| 5,526,287 | 6/1996 | French | 364/550 |
| 5,530,235 | 6/1996 | Stefik et al. | 235/492 |
| 5,548,730 | 8/1996 | Young et al. | 395/280 |
| 5,559,965 | 9/1996 | oOztaskin et al. | 395/284 |
| 5,566,346 | 10/1996 | Andert et al. | 395/828 |
| 5,574,915 | 11/1996 | Lemon et al. | 395/700 |

*Primary Examiner*—Hezron E. Williams
*Assistant Examiner*—Jay L. Politzer
*Attorney, Agent, or Firm*—J. Nevin Shaffer, Jr.; Shaffer & Culbertson

[57] ABSTRACT

A modular water quality measurement apparatus and method includes a sealed or unsealed housing with a universal sensor interface cap (12) and mechanical and electrical sensor connections (14) for receiving removably attachable sensors (16 or 16'). Each of the mechanical and electrical sensor connections (14) are individually electrically connected to a programmable motherboard (20) within the housing. Sensor daughterboards (22) are removably attached to the motherboard (20) corresponding to individual sensors (16 or 16') connected to the universal sensor interface cap (12). Further, removably attachable input/output daughterboards (24) are electrically connected to the motherboard (20) for accommodating various serial interface types and software is provided for collecting information from the sensors (16 or 16') and transmitting the information through the input/output daughterboards (24) for manipulation by a user. Additionally, a removably attachable plug (26) is provided for sealing mechanical sensor connections (14) which are not sealed by sensors (16 or 16'). The software includes product software for gathering information from the sensors (16 or 16'), learnable sensor driver software for directing the product software and manipulating gathered information, and learnable interface software for transmitting the gathered information for further manipulation by various interface devices. In another preferred embodiment, sensor (16') while including sensing sensor element (28) as does sensor (16), further includes a sensor PCB (32) thereby eliminating the need for sensor daughterboards (22). Sensor (16') is connected to motherboard (20) by means of sensor interface bus connections (38) thereby enabling the product to be more compact and efficient.

8 Claims, 7 Drawing Sheets

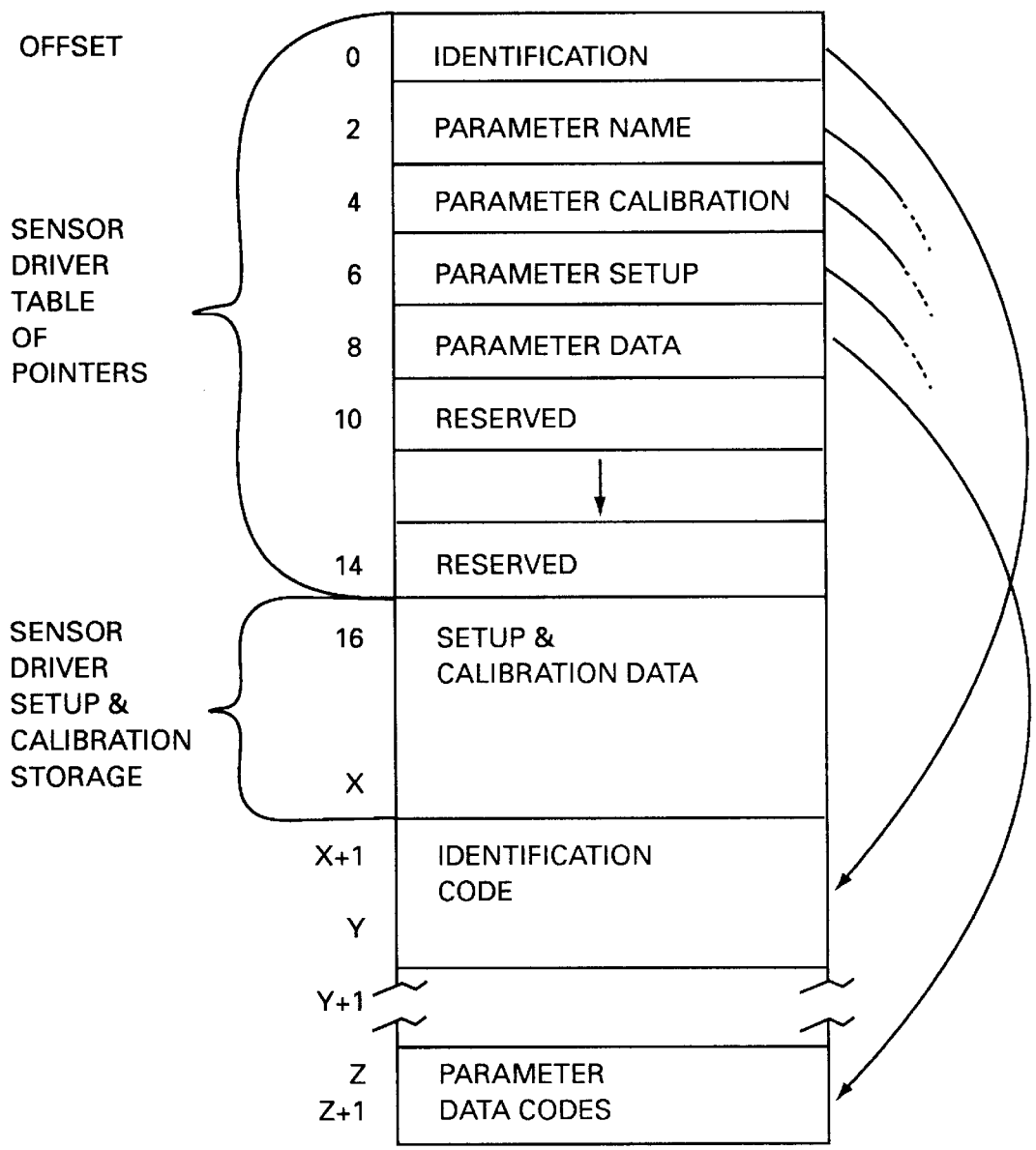
Figure 6  SENSOR DRIVER MEMORY STRUCTURE
(example in INTEL 80x86 NEAR ADDRESS SIZES)

Figure 7  PRODUCT SOFTWARE TABLE STRUCTURE
(example in INTEL 80L188EB INTERRUPT VECTOR TABLE)
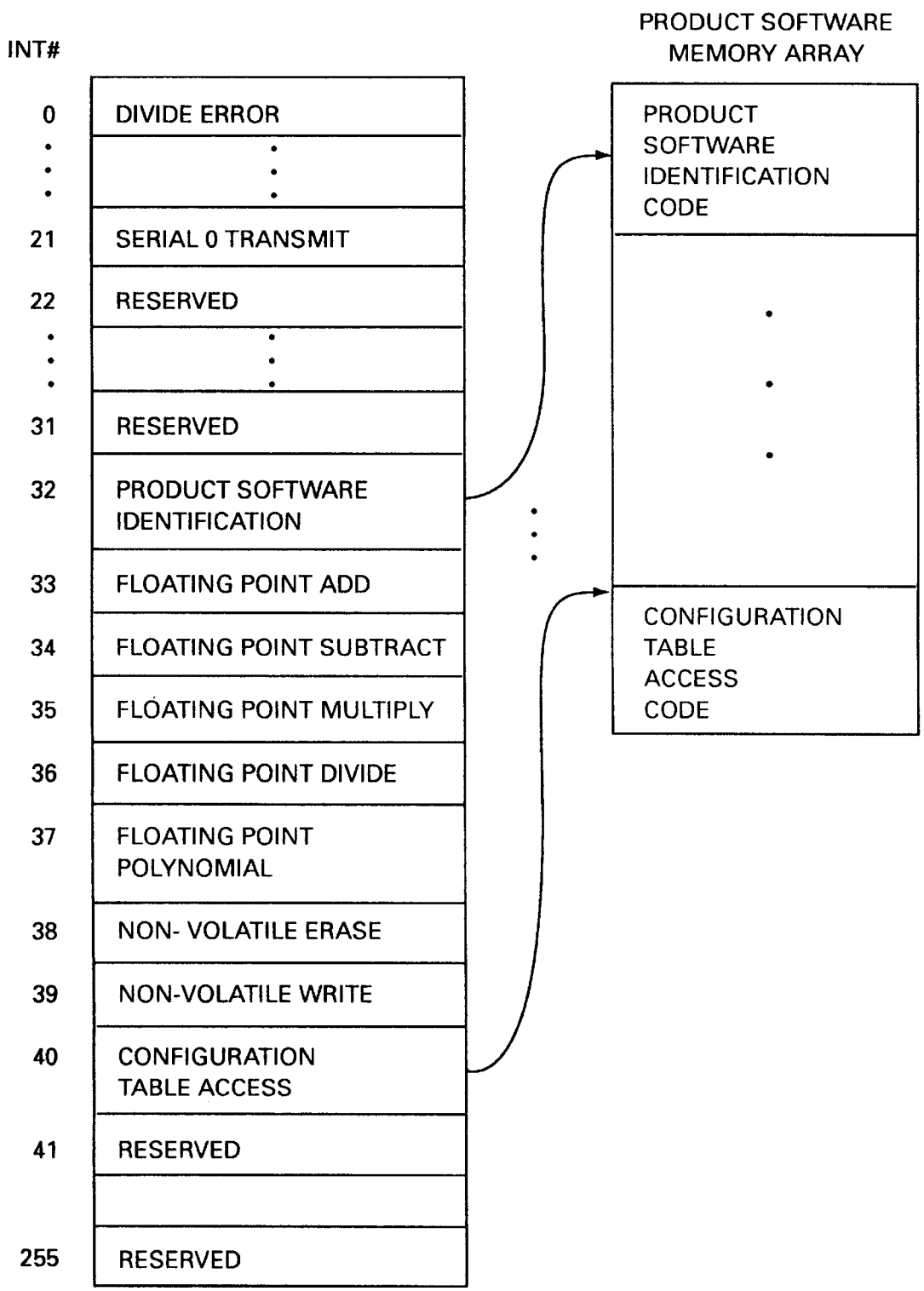

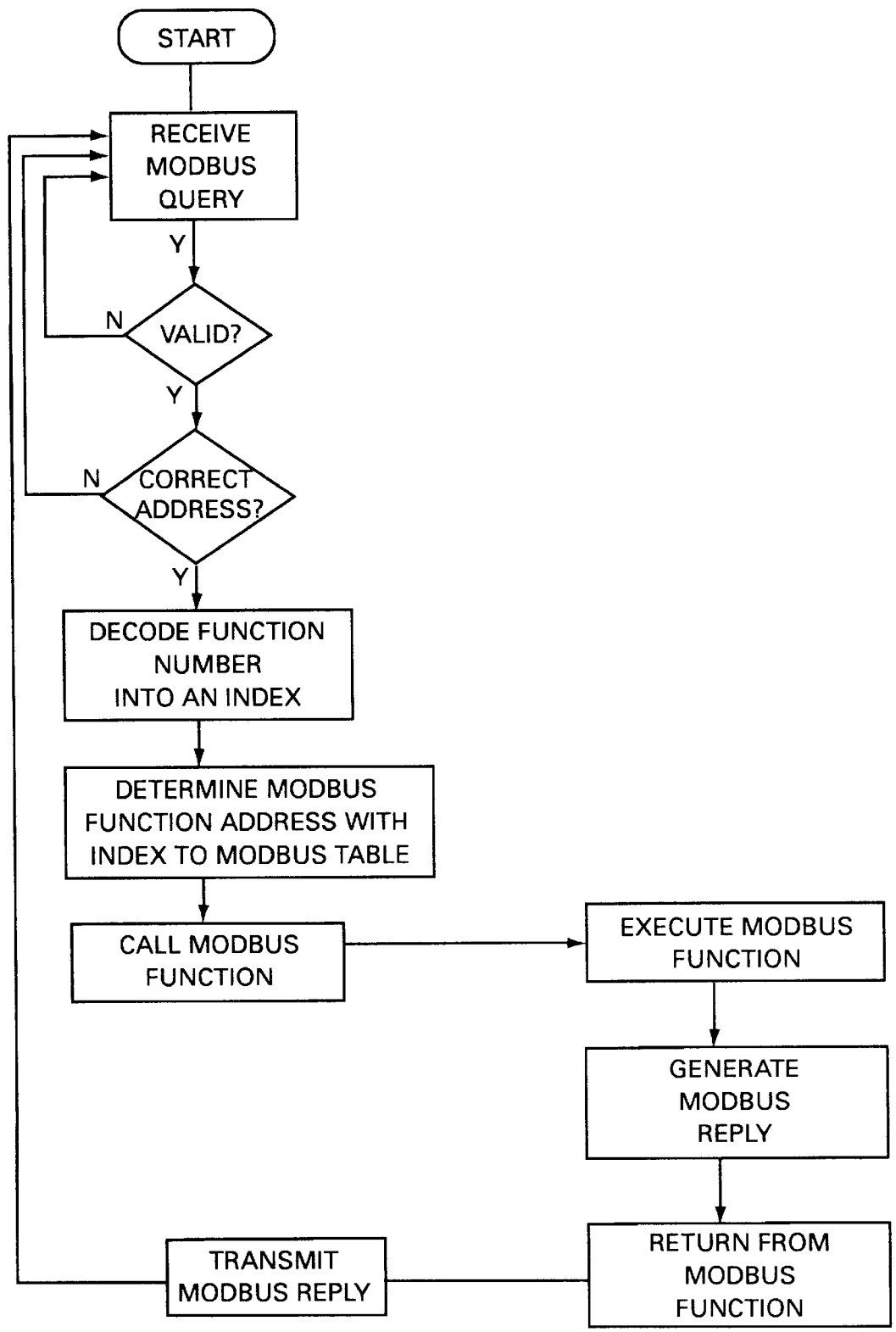
Figure 8 — GENERAL FLOW CHART FOR PRODUCT SOFTWARE TO MODBUS

MODULAR WATER QUALITY APPARATUS AND METHOD

This application is a continuation of application Ser. No. 08/608,710, filed Feb. 29, 1996, now abandoned.

BACKGROUND OF THE INVENTION

This invention relates to a modular water quality measurement sensor system and in particular to a modularized sensor apparatus and method.

Both manual and electrical mechanical devices have been known in the art for quite some time for sensing desired information from the environment. In particular, as to water monitoring and measuring devices, an example of prior art electrical mechanical devices is disclosed in D'Aoust, U.S. Pat. No. 4,662,210, which utilizes a probe inserted in the water and connected by cable to a control housing capable of receiving and analyzing a variety of data from the sensor so as to provide a display of desired information such as dissolved gas pressure, barometric pressure, temperature, percent saturation, and difference between total dissolved gases and barometric pressures. Other types of data have been deemed needed and sensors have been developed to provide the data. Certainly, as technology progresses, the ability to sense other parameters will become practical and other sensors will be developed. As populations increase and water supplies decrease, the need for managing water resources becomes more and more critical. This can only be done when a complete analysis of the quality of the water being utilized is known.

State of the art water quality products are comprised of four basic elements. There is a printed circuit board (PCB) containing serial interface (I/F) circuitry, and I/F circuitry for all compatible sensors. The serial I/F circuitry is generally an RS232 or SDI-12 serial I/F to a computer, data logger, or other serial device, but cannot be changed, however, without modifying the PCB. Further, the sensor I/F circuitry is dedicated to specific functions and cannot adapt to different sensors without substantial modification. The second element is PCB-resident software containing the complete set of measurement control and computational algorithms for all compatible sensors. The major problem here is that the software cannot accommodate sensors for which the PCB cannot interface. The third element is the mechanical connections allowing the sensors to be attached to the water testing product in dedicated locations. Most products today constrain sensors to dedicated locations through mechanical mounting methods. Others limit sensors to dedicated locations by varying the electrical connector compatibility. Nonetheless, there are a wide variety of sensors capable of measuring various water quality parameters that are available. Currently, if a new sensor is to be added to a product, the original product has to undergo major modifications, including wholesale modification of the PCB. As a partial solution, some products have been designed to allow for the installation and removal of PCBs which interface to specific sensors.

Drawbacks to the sensors known in the art, however, remain and are numerous. Today, prior art sensors and sensor products have serial input/output (I/O) which are a dedicated PCB function which cannot be replaced without significant PCB rework. Further, serial I/O data interpretation requires the PC, data logger, or other serial I/F device to understand the sensor nuances. Modifications and/or updates to the water quality product may require updates to the PCB, data logger, or serial I/F to understand these sensor nuances. Still further, sensors cannot be updated without significant rework of one or more of the following standard items, that is the PCB, the sensor mechanical/electrical attachment, and/or the software. Also, sensors cannot be added to a product without significant rework of one or more of the following, including the PCB, the sensor mechanical/electrical attachment, and/or the software. Most disturbingly, users today must buy functionality which they do not need and may not want. That is, lower end products contain a full range PCB and software which has the capability of presenting data and menu options for features which are not installed on the product. This situation causes the manufacturer to reduce profits on minimally equipped products and attempt to recover on fully equipped products. The end result is the user becomes confused as to what the product can or cannot do and this confusion costs the user time and money determining configuration capabilities and functionalities of the purchased product.

Thus, there is a need in the art for providing a sensor system for enabling a single product to be compatible with multiple sensors, multiple interfaces, and multiple sensor circuitry so that a single product can be easily and economically configured to a user's requirements and which is capable of enabling upgraded additions of sensors yet to be desired or developed. It, therefore, is an object of this invention to provide an improved sensor system for providing updates and additions of sensors without requiring significant rework of the PCBs, sensor mechanical/electrical attachments, or software.

SHORT STATEMENT OF THE INVENTION

Accordingly, the modularized sensor system of the present invention includes a sealed or unsealed housing with a universal sensor interface cap. The universal sensor interface cap contains mechanical sensor connections for receiving uniform, removably attachable, sensors. Each of the mechanical sensor connections are individually connected to a remotely-programmable motherboard within the housing. Additionally, sensor daughterboards are provided which are removably attachable to the motherboard and which correspond to individual sensors connected to the universal sensor interface cap. Removably attachable input/output daughterboards are connected to the motherboard for accommodating various serial interface types and software is provided for collecting information from the sensors and transferring the information through the input/output daughterboards for manipulation by a user.

The universal sensor interface cap also includes plugs for sealing sensor connections not sealed by sensors. The sensors include a sensing element, known or hereafter developed, and a sealed connector conformed to fit and seal the mechanical sensor connections in the universal sensor interface cap.

Another preferred embodiment of the invention includes a uniform sensor with a PCB, essentially a sensor daughterboard, installed inside the sensor itself instead of attached to the motherboard. In this embodiment, the connection to the universal sensor interface cap is direct, but the attachment of the "sensor daughterboard" to the motherboard is now through the universal sensor interface cap.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 6 is a sensor driver memory chart;

FIG. 7 is a product software table structure; and

FIG. 8 is a flow chart for product software to MODBUS.

DETAILED DESCRIPTION OF THE PREFERRED EMBODIMENTS

Figure 1:
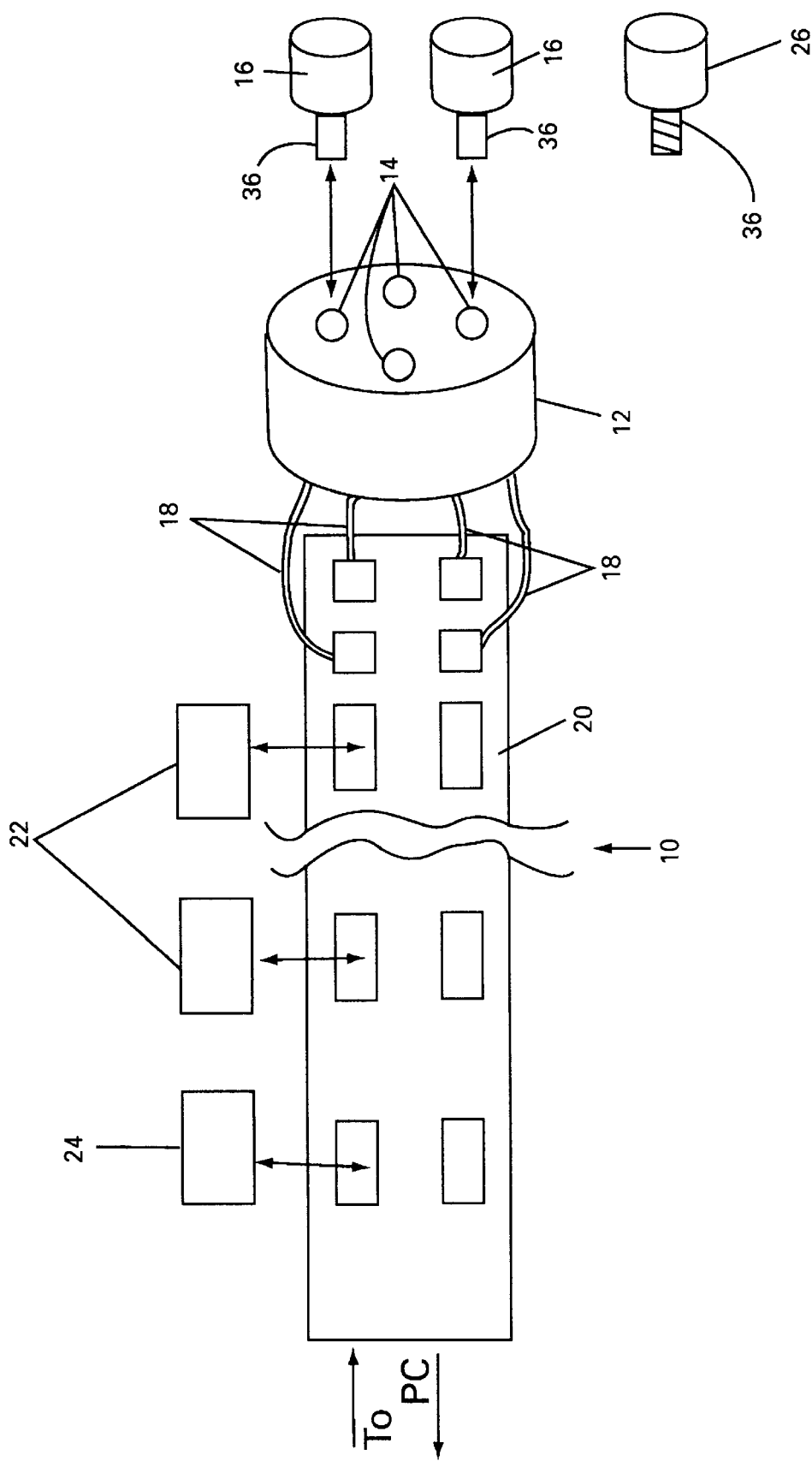
FIG. 1 is a plan view of a preferred embodiment of the modularized sensor system of the present invention in exploded form without the sealed housing.

The preferred embodiments of the present invention are illustrated by way of example in FIGS. 1–8. With specific reference to FIG. 1, a modularized sensor 10 includes a sealed housing (not shown) to which is attached a universal sensor interface cap 12. A plurality of mechanical sensor connections 14 are provided in universal sensor interface cap 12. Removably attachable uniform sensors 16 are conformed so as to fit within and to seal mechanical sensor connections 14. Each of the mechanical sensor connections 14 are individually connected by sensor connections 18 to a programmable motherboard 20 conformed to be located within the sealed housing (not shown).

Also illustrated are sensor daughterboards 22 and input/output daughterboards 24 designed to be removably attachable to motherboard 20. Software (not shown and discussed more fully hereafter) for collecting information from the sensors and transferring this information through the input/output daughterboards 24 for manipulation by a user, is also included. FIG. 1 also shows a removably attachable plug 26 designed to seal mechanical sensor connection 14 whenever there are more mechanical sensor connections 14 than there are sensors 16.

Figure 2:
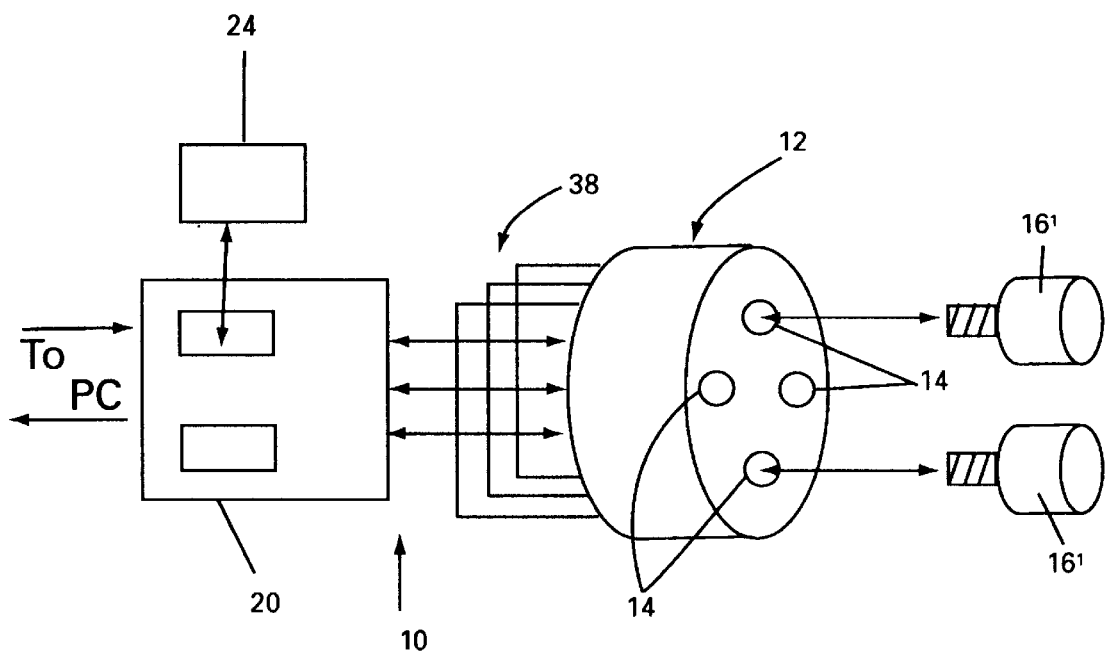
FIG. 2 is a plan view of another preferred embodiment of the modularized sensor system of the present invention in exploded form without the sealed housing.
Figure 3:
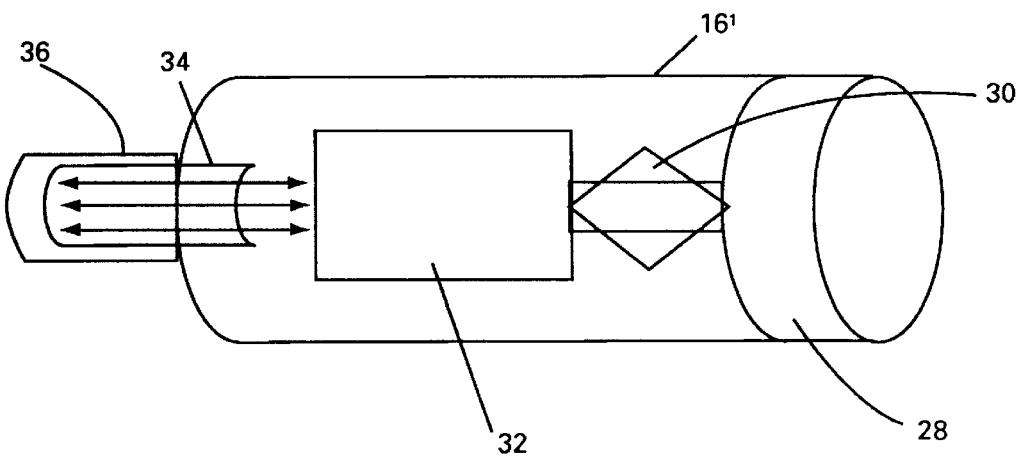
FIG. 3 is a partial section view of the sensor of FIG. 2 showing the sensor PCB within the sensor itself.

Referring now to FIGS. 2 and 3, another preferred embodiment of the present invention is illustrated. In this embodiment, uniform removably attachable sensor 16' is a "smart" sensor. That is, it contains the usual sensor sensing element 28, now known or to be developed, connected by electrical connections 30, known in the art, to a sensor PCB 32 connected by electrical connection 34, known in the art, to sealed connector 36 conformed to just fit within and seal and make electrical connection with mechanical sensor connections 14.

Further, in this embodiment, sensor connections 18 are replaced with sensor interface bus connection 38. Sensor interface bus connection 38 is connected to motherboard 20. Motherboard 20 includes input/output daughterboards 24. This embodiment also includes software for collecting information from the sensors and transferring the information through the input/output daughterboards 24 for manipulation by a user.

To restate the problem, prior art sensors, including water quality sensors, require significant rework of the PCBs, sensor mechanical/electrical attachments, and software whenever sensors are updated or additions are made. If a sensor changes, the manufacturer currently must not only redesign the PCB, mechanical/electrical attachments, and software unique to that sensor, but the manufacturer must also rework the unchanged portions of the product because all prior art PCB circuitry is grouped together, all prior art mechanical/electrical attachments are unique, and all prior art software measurement and computation functions are grouped together. Further, updating or adding sensors to prior art water quality systems may require significant rework of the software run on the personal computer (PC), data logger, or other serial interface devices in order to communicate, properly interpret, and present the sensor information to the user.

The invention solves these problems by providing common interfaces for the sensor mechanical/electrical attachment, individual PCBs for sensor circuitry, individual sensor software modules to deal with the unique sensor interface measurements and computation algorithms, and "learnable" software interfaces from the individual sensor driver software modules as well as from the product software interface to the PC, data logger, and other serial interface devices. As a result, and as will be more fully described hereafter, by way of the present invention the manufacturer merely needs to focus on the effort required to develop the updated or added sensor, the individual sensor PCB, and the unique sensor software. The manufacturer, by the present invention, is spared the burden of reworking the entire product PCB and software and multiple mechanical/electrical attachments. Further, the manufacturer and/or user is spared the incompatibility and/or update burden of reworking software for the PC, data logger, or other serial interface device due to the "learnable" software interface.

The four solution elements described above are more particularly described hereafter. As illustrated in FIGS. 1 and 2, the primary mechanical attachment problem is solved by this invention by the universal sensor interface cap 12. The cap 12 provides mechanical support for the sensors 16 and 16', by mating to threaded collars (not shown) on sensors 16 and 16'. Any other appropriate mating method known in the art may also be utilized. Universal sensor interface cap 12 also physically supports the motherboard 20 by any means known in the art such as an angle bracket-type configuration (not shown). Additionally, universal sensor interface cap 12 partially solves the electrical attachment problems of the prior art, that is, cap 12 contains connectors (not shown) for attachment to the sensors 16 and 16'. Additionally, as illustrated, sensor connections 18 and sensor interface bus 38, discussed more fully hereafter, make the attachment to the motherboard 20.

Motherboard 20 contains input/output connector, power supplies, microprocessor, non-volatile memory, real-time clock, shared analog components (analog-to-digital converter, voltage reference, etc.), and other glue logic necessary to provide a general purpose measurement and computation platform, as is known in the art. The motherboard 20 completes the sensor electrical solution to prior art problems. That is, sensor connections 18 and sensor interface bus connection 38 provide a method of connecting the sensors 16 and 16' to the motherboard 20. The figures show four sensor connections 18 and sensor interface bus connections 38, but obviously, any physically practical number may be implemented. Within motherboard 20, traces are routed from the sensor connections 18 to the sensor daughterboards 22. This wiring method greatly simplifies unique system configurations in that each sensor connection 18 is routed to one and only one sensor daughterboard 22 positioned on the motherboard 20.

Figure 4:
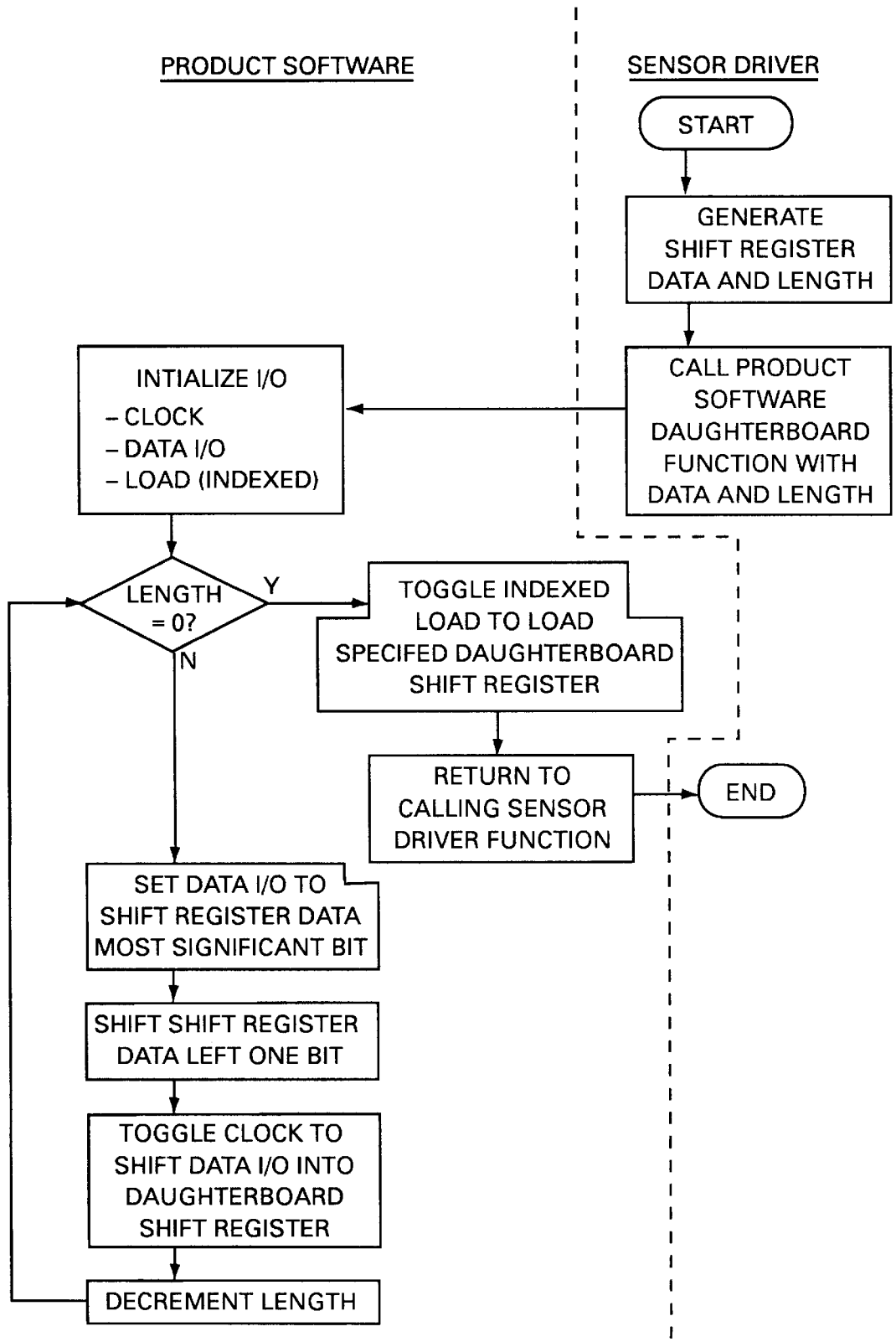
FIG. 4 is a flow chart for product software to daughterboards.
Figure 5:
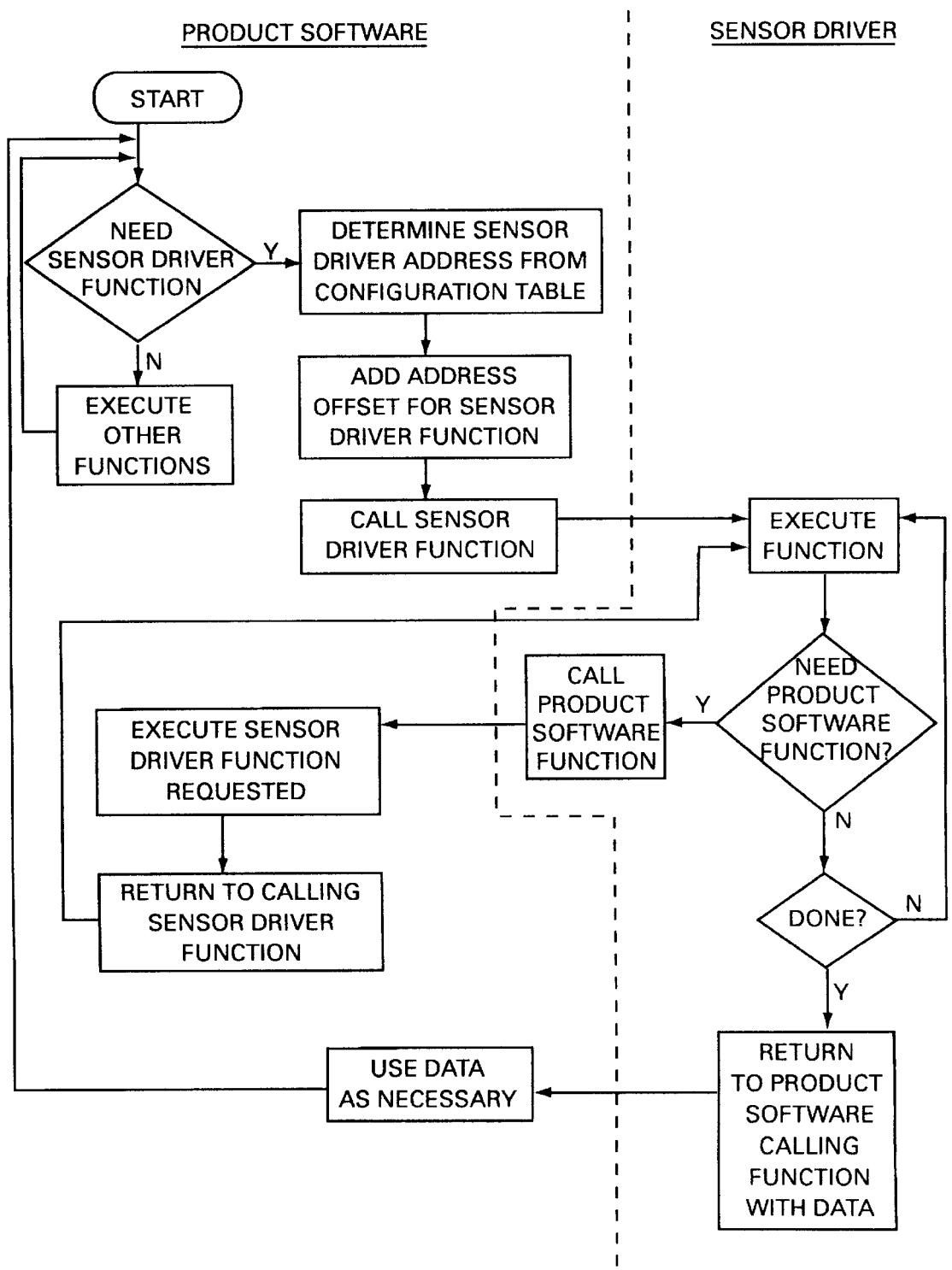
FIG. 5 is a flow chart for product software to sensor driver.

The motherboard 20 under the control of the product and sensor driver software (see FIG. 4), discussed more fully hereafter, sequences the measurement of each sensor 16 or 16' via interface signals from the microprocessor to a second connector between the motherboard 20 and each sensor daughterboard 22. The microprocessor on the motherboard 20 is digitally interfaced to each sensor daughterboard 22 via a serial shift register. The microprocessor clocks the shift register and then loads the shift register output latches to present digital controls to the sensor daughterboard 22. The shift register approach allows the sensor daughterboards 22 to stay "general purpose" since any practical shift register depth is easily supported. Using these digital shift register outputs, the microprocessor provides the control signals necessary to properly excite, sequence, and measure the sensor 16 and 16' outputs. For example, the microprocessor is able to provide signals to all sensor daughterboards 22 which enables one and only one sensor daughterboard 22 to supply its analog signal to the analog-to-digital converter for digitization. This process can be accomplished in any way known in the art and as illustrated in FIG. 4.

The input/output connection to a PC, data logger, or other serial device is provided by motherboard 20 passing connections from an input/output connector to the input/output daughterboard 24. A microprocessor, as is known in the art, contained on the motherboard 20 then interfaces to the input/output daughterboard 24. In this manner, serial input/output is established by the microprocessor, but the physical electrical interface depends upon the hardware used by the input/output daughterboard 24.

As a result, the serial interface type can be changed by replacing input/output daughterboard 24 with one of several styles, such as RS232, SDI-12, RS422, RS485, or any other preferred interface. The present invention, by means of input/output daughterboards 24 as herein described, allows the same base product to connect to newer equipment without sacrificing compatibility with older established installations.

In a preferred embodiment, sensor daughterboards 22 connect to the motherboard 20 in order to complete the sensor connection and to get control information from the microprocessor. Under microprocessor control, as explained earlier, the sensor daughterboard 22 provides an analog voltage or digitized bit stream representation of the sensor measurement. The circuitry (not shown) on the sensor daughterboards 22 varies among sensor types, as is known in the art. The circuitry which is appropriate for a dissolved oxygen sensor, for example, is not appropriate for a conductivity sensor. The circuitry on the sensor daughterboard 22, in this invention, encapsulates the lowest level of unique circuitry needed to operate the sensor 16 and 16'. Sensor daughterboards 22 are developed in order to be compatible with sensors for determining conductivity, dissolved oxygen, pH, redox, ammonium, nitrate, turbidity, and isolated analog voltage inputs, as well as any other desired input developed now or hereafter.

The sensors, 16 and 16', are comprised of a sensor sensing element 28 attached to a sealed connector 36 with a threaded collar (not shown). The sensor sensing elements 28 are no different than the sensing elements known in the art or hereafter developed. The sealed connectors 36 are conformed so as to provide the common mechanical and electrical interface disclosed in the invention. That is, all sensors 16 and 16' are uniform and share a common connector and the same threaded collar, for example, but the sensing elements 28 can be as varied as the types of measurements to be made.

Referring now to FIGS. 4–8, the present invention requires software for collecting information from the sensors 16 and 16' and transferring the information through the input/output daughterboards 24 for manipulation by a user on PCs and so forth. Any suitable software that accomplishes that is appropriate. Nonetheless, discussion of the type of software is provided for a full understanding of the invention. In general, the software utilized by the invention includes three types, "learnable" sensor driver software, product software, and "learnable" interface software. Sensor driver software contains the algorithms needed to measure the sensor 16 and 16' by controlling the sensor daughterboard 22. Because further processing is generally required for all sensors 16 and 16', these computation algorithms are encapsulated within the sensor driver software. The product software is the software on the motherboard 20 which provides software services such as I/O, multiply, divide, etc., as is known in the art. Further, the product software contains a configuration table in non-volatile memory which points to the location of installed sensor drivers (see FIG. 5). Initially, the configuration section is empty as no sensors 16 or 16', daughterboards 22, or sensor driver software have been installed. After determining the product configuration, a user will install the appropriate sensors 16 and 16' into the universal sensor interface cap 12, install the appropriate sensor daughterboard 22 into an available motherboard 20 location, and install the selected input/output daughterboard 24. At that point, the product must then be attached to a device to download the sensor drivers for the selected sensors 16 and 16'. This process is most easily done by a PC using an XMODEM type of protocol, but any download operation could be used. The product software saves the sensor driver into an unused location within the non-volatile memory on the motherboard 20 and updates the configuration table.

A primary requirement for the sensor driver is that it be "learnable." That is, the product software need not know any unique capability of the sensors 16 or 16', but must be able to gather all information necessary to gather data from the sensors 16 or 16', display data to the user, execute sensor setup, and execute sensor calibration. For this embodiment, parameter passing may follow any conventional software protocol, pointer to global, stack reference, register based, etc., but the beginning of each sensor driver must contain a table which contains pointers to the following functions:

Identification: The sensor driver must state the sensor driver title and version.

Parameter number, name(s). and unit(s): The sensor driver must report the number of parameters which can be produced by the sensor 16 or 16' as well as the parameter names and units. The sensor 16 or 16' attached to the sensor daughterboard 22 may produce multiple values which the product software must understand. For example, a conductivity sensor is only one sensor, but conductivity, specific conductance, salinity, and total dissolved solids are parameters which may be computed from this one sensor. Additional values supplied by this function include display format, minimum in range value, maximum in range value, suitability as an X-axis value on an X-Y graph, and calibration capability and range.

Parameter calibration: After learning the calibration capability, the product software, under user direction, must call the sensor driver calibration function for the specified parameter. The sensor driver will compute new calibration constant(s) for the given parameter.

Parameter setup: Sensors 16 or 16' may require specific setup information be available. The product software will call this function, under user direction, to gather questions to ask the user. After the user completes the questions, the sensor driver will adjust the setup information which will be applied to the next setup request and data request.

Parameter data: After learning the parameter types, the product software may request data from any parameter supplied by the sensor driver. The product software will pass an index within the range 0 to number of parameters minus one to specify which data value is desired. The sensor driver described above can be established by any means and methods known in the art and as illustrated in FIG. 6.

In order to execute the above functions, the sensor driver requires access to certain product software capabilities. Granting access to these capabilities within the product software helps maintain small sensor drivers as well as preventing updates to the motherboard 20 and product software from requiring updates to the sensor drivers. For this embodiment, the product software provides a fixed location table in memory to pointers to product software services for the sensor driver to call. The following services, at a minimum, are required:

Identification: The product software must state its driver interface version. This allows the sensor driver to downgrade capability if necessary to be compatible with possibly older and obsolete product software driver interface versions.

Math functions: The location of the floating point add, subtract, multiply, divide, polynomial functions, etc. must be specified.

Non-volatile memory erase/write: The sensor driver must be capable of maintaining its calibration constants.

Configuration table read access: The sensor driver may require data from another sensor. For example, specific conductance requires temperature data for temperature compensation. The conductivity sensor driver, when asked to produce specific conductance, must be able to locate and call the temperature sensor driver in order to complete its computation.

The product software table structure can be that of any known in the art and as illustrated in FIG. 7.

The "learnable" interface describes the communication between the motherboard 20 and a PC, data logger, or the like, not shown and known in the art. Just as in the sensor drivers, the present invention allows a user to attach products equipped with different sensor configurations to a PC, for example, which allows the PC to gather all information necessary to collect data from the product, display data to the user, execute sensor 16 or 16' setup, and execute sensor 16 or 16' calibration.

For this embodiment, the product executes a MODBUS protocol (see FIG. 8), but any similar protocol may be utilized, with several custom user defined functions. MODBUS is chosen due to a well-defined timing and structure, but the user-defined functions are necessary to deal with the differences between programmable logic controllers and water quality instruments. MODBUS is a master/slave protocol. The PC acts as a master while the product operates as a slave. Because the interface software must be learnable, the following functions are required for "learnability":

Identification: The product must state its title and product software version.

Parameter number name(s), and unit(s): The product software must report the number of parameters which can be produced by all the installed sensors 16 and 16' as well as the parameter names and units. This output is essentially a compilation of the installed sensor driver outputs. The data is passed through to the PC. Additional values supplied by this function include display format, minimum in range value, maximum in range value, suitability as an X-axis value on an X-Y graph, and calibration capability and range.

Parameter calibration: After learning the calibration capability, the PC software, under user direction, must call the product software calibration function for the specified parameter. The product software via the sensor driver will compute new calibration constant(s) for the given parameter.

Parameter setup: Sensors 16 or 16' may require specific setup information be available. The PC will call this function, under user direction, to gather questions to ask the user. After the user answers the questions, the product software via the sensor driver will adjust the setup information which will be applied to the next setup and data request.

Parameter data: After learning the parameter types, the PC may request data from any parameter supplied by the product software via sensor drivers. The PC will pass an index within the range 0 to number of parameters minus one to specify which data value is desired. The product software will translate this index into the appropriate sensor driver and index to specify which data value is desired.

Logging status: The product may have logging capability which can be accessed via the PC. The product returns a table containing, at a minimum, the log file name, setup date, start date, stop date, interval, and size. In addition, this function returns the amount of memory and battery capacity remaining as well as the expected run out given current usage.

Logging setup: The PC can specify a new logging operation to execute or modify an existing setup.

Logging dump: The PC can specify a logging file to dump. This dump can be based on the entire file or by specifying a start/stop date. All other MODBUS transactions can be executed within a single MODBUS master/slave transaction. This dump function, due to the volume of data, is broken into discrete blocks. The PC requests a block and the product responds with that block. After manipulating this block, the PC may request a retransmission or request the next block. This process continues until the product returns a "no more data" block or the PC aborts the dump.

As illustrated in FIGS. 2 and 3, another preferred embodiment of the present invention is illustrated. In this embodiment, universal sensor interface cap 12 still has common connectors 14, but now the wires are tied together in a common sensor interface bus 38 arrangement. This bus 38 arrangement is analogous to the microprocessor connections to sensor daughterboards 20 of the first embodiment. The universal sensor interface cap 12 and sensor interface bus 38 solves the common mechanical/electrical attachment requirement. In this embodiment, as compared to the first, the motherboard 20 loses the multiple sensor daughterboards 22 and locations and the sensor connections 18 to be replaced by a single sensor interface bus 38 connection. All other attributes about the motherboard as previously described remain unchanged.

The sensor PCB 32, in this embodiment, is essentially a sensor daughterboard which is installed inside the "smart" sensor 16' instead of being attached to the motherboard 20. The connection to the sensing element 28 is now direct, but the attachment to the motherboard 20 is now through the universal sensor interface cap 12 and the sensor interface bus connections 38. All other attributes of the sensor daughterboards 22, as previously described, are shared with the sensor PCB 32.

The sensor sensing element 28 is similar to the sensors 16 except that direct connection to the sensor board is within the sensor 16' and not distributed through universal sensor interface cap 12 and motherboard 20 to a daughterboard 22. Otherwise, the sensing elements 28 are no different than sensing elements 28 described in the prior embodiment. Likewise, the product software, sensor driver, and learnable interface are identical to that described above.

As can be appreciated from the above description, a method of modularized sensing includes providing a sealed housing with a universal sensor interface cap 12. The housing can be unsealed, as well, and is any type known in the art for containing and/or supporting the subject components. The universal sensor interface cap 12 is provided with mechanical sensor connections 18 for receiving removably attachable sensors 16. The mechanical sensor connections are individually connected to a programmable motherboard 20 within the housing. Likewise, removably attachable sensor daughterboards 22, corresponding to individual sensors 16 connected to the universal sensor interface cap 12, are attached to the motherboard 20. Further, removably attachable input/output daughterboards 24 are attached to the motherboard 12 for accommodating various serial interface types. Next, software is provided for collecting information from the sensor 16 or 16' and transmitting the information through the input/output daughterboards 24 for manipulation by a user. The user determines the desired product configuration of the sensor apparatus, installs the appropriate sensors 16 or 16' into the universal sensor interface cap 12, installs the appropriate sensor daughterboard 22 into an available motherboard 20 location, and installs the appropriate input/output daughterboard 24. Next, the sealed housing is attached to an interface device for downloading sensor driver software for the selected sensors 16 or 16' and the sensor driver software is saved, by means of product software, within the memory on the motherboard 20. At this point, the user operates the sensor, the data is collected within the product, and the gathered information is transmitted through the input/output daughterboards 24 for manipulation by the user. The method also includes using a removably attachable plug 26 for sealing sensor connections 14 not sealed by sensors 16 or 16'.

The above described preferred embodiments are intended to illustrate the principles of the invention, but not to limit the scope of the invention. For example, while the particular invention is directed to modular water quality measurement sensor systems, it applies equally as well to other sensor apparatus and methods as well. Further, various other embodiments and modifications to these preferred embodiments may be made by those skilled in the art without departing from the scope of the following claims.

I claim:

1. A modularized sensor apparatus comprising:
   (a) a housing with a universal sensor interface cap;
   (b) mechanical sensor connections in said universal sensor interface cap for receiving uniform, removably attachable, sensors, with each of the mechanical sensor connections individually connected to a programmable motherboard within said housing;
   (c) bi-directional sensor daughterboards removably attached to the motherboard, corresponding to individual sensors connected to the universal sensor interface cap; and
   (d) software for collecting information from said sensors and transferring the information for manipulation by a user, said software comprising product software for gathering information from the sensor(s), sensor driver software for directing the product software and manipulating gathered information, and interface software for communicating with various interface devices and transmitting the gathered information for further manipulation wherein:
      i. said product software further comprising a product software services table for said sensor driver software to call comprising identification services, nonvolatile memory write services, and configuration table read access:
      ii. said sensor driver software further comprising a sensor driver software table comprising sensor driver title and version identification, parameter number, name(s), and unit(s), parameter calibration, parameter setup, and parameter data; and
      iii. said interface software further comprising the following functions: identification of product title and software version, parameter number, name(s), and unit(s) of said product software, parameter calibration, parameter setup, parameter data, login status, login setup, and login dump.

2. The apparatus of claim 1, further comprising removably attachable bi-directional input/output daughterboards connected to the motherboard for accommodating various serial interface types.

3. The apparatus of claim 1, further comprising removable, attachable plugs for sealing sensor connections not sealed by sensors.

4. The apparatus of claim 1, wherein the uniform, removably attachable, sensors further comprise:
   (a) a sensor sensing element; and
   (b) a sealed connector conformed to fit and seal the mechanical sensor connections in the uniform, sensor interface cap.

5. The apparatus of claim 1, wherein the bidirectional sensor daughterboards further comprise circuitry, appropriate to specific sensor type, at the lowest level necessary to operate the sensor.

6. In a water quality sensing device of the type used to sense physical and chemical properties of water with sensors, a modularized sensor apparatus comprising:
   (a) a sealed housing with a universal sensor interface cap;
   (b) mechanical sensor connections in said universal sensor interface cap for receiving uniform, removably attachable, sensors with each of the mechanical sensor connections individually connected to a programmable motherboard within said housing, the sensors comprising a sensor sensing element and a sealed connector conformed to fit and seal the mechanical sensor connections in the universal sensor interface cap;
   (c) bi-directional sensor daughterboards removably attached to the motherboard corresponding to individual sensors connected to the universal sensor interface cap;
   (d) software for collecting information from said sensors and transferring the information for manipulation by a user, said software comprising product software for gathering information from the sensor(s), sensor driver software for directing the product software and manipulating gathered information, and interface software for communicating with various interface devices and transmitting the gathered information for further manipulation wherein:
      i. said product software further comprising a product software services table for said sensor driver software to call comprising identification services nonvolatile memory write services and configuration table read access;

ii. said sensor driver software further a sensor driver software table comprising sensor driver title and version identification, parameter number, name(s), and unit(s), parameter calibration, parameter setup, and parameter data; and iii. said interface software further comprising the following functions: identification of product title and software version, parameter number, name(s), and unit(s) of said product software, parameter calibration, parameter setup, parameter data, login status, login setup, and login dump; and (e) removably attachable plugs for sealing sensor connections not sealed by sensors.

7. The apparatus of claim 6 further comprising removably attachable bi-directional input/output daughterboards connected to the motherboard for accommodating various serial interface types.

8. The apparatus of claim 6, wherein the bi-directional sensor daughterboards further comprise circuitry, appropriate to the specific sensor type, at the lowest level necessary to operate the sensor.

\* \* \* \* \*